United States Patent
Park et al.

[11] Patent Number: 5,571,936
[45] Date of Patent: Nov. 5, 1996

[54] INTERMEDIATES FOR THE SYNTHESIS OF 16-PHENOXY-PROSTATRIENOIC ACID DERIVATIVES AND A PREPARING METHOD THEREOF

[75] Inventors: Hokoon Park; Sun Ho Jung; Yong Sup Lee; Ki Hong Nam, all of Seoul, Rep. of Korea

[73] Assignee: Korea Institute of Science and Technology, Seoul, Rep. of Korea

[21] Appl. No.: 316,205

[22] Filed: Sep. 30, 1994

[51] Int. Cl.$^6$ .................................................. C07C 69/587
[52] U.S. Cl. ...................... 560/121; 549/214; 549/415; 549/473; 554/119; 554/140; 554/148; 556/440
[58] Field of Search ........................... 560/121; 554/119, 554/140, 148; 549/415, 473, 214; 556/440

[56] References Cited

U.S. PATENT DOCUMENTS 3,985,791 10/1976 Muchowski et al. .
4,178,475 12/1979 Van Horn et al. .
4,600,785 7/1986 Cooper et al. .

OTHER PUBLICATIONS

Acta. Chemica Scandinavia B 36 (1982) 179–185.
J. Am. Chem. Soc. 1990, 112, 8042–8047.
J. Med. Chem. 1991, 24, 1353–1359.
J. Org. Chem. 1980, 45, 4740–4747.
Tetrahedron Letters No. 18, 1975, 1509–1512.
Tetrahedron Vo. 35, pp. 2931–2938, 1979.
Tetrahedron Letters No. 51, 1975, 4615–4618.

*Primary Examiner*—Nicky Chan
*Attorney, Agent, or Firm*—Darby & Darby, P.C.

[57] ABSTRACT

Intermediate compounds represented as formula (I) useful for the synthesis of 16-phenoxy-prostatrienoic acid derivatives and a preparing method thereof are disclosed.

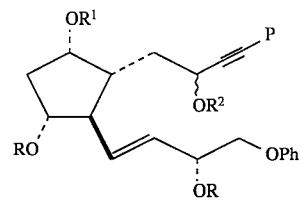

wherein R is tetrahydropyranyl, tetrahydrofuranyl, 2-ethoxyethyl, 3-t-butyldimethylsilyl triisopropylsilyl or triethylsilyl group; $R^1$ and $R^2$ are independently hydrogen or ester-forming group; P is hydrogen, trimethylsilyl or tri-n-butyltin; and wavy line means epistereoisomeric mixture.

3 Claims, No Drawings

INTERMEDIATES FOR THE SYNTHESIS OF 16-PHENOXY-PROSTATRIENOIC ACID DERIVATIVES AND A PREPARING METHOD THEREOF

BACKGROUND OF THE INVENTION

1. Field of the Invention

This invention relates to intermediate compounds useful for the synthesis of 16-phenoxy-prostatrienoic acid derivatives and a preparing method thereof. Because 16-phenoxy-9-keto-prostatrienoic acid derivatives (enprostil) possess antisecretory activity, they are useful in treating gastrointestinal disorders. 16-Phenoxy-9α-hydroxyprostatrienoic acid derivatives (fenprostalene) are useful as luteolytic agents in female mammals, since they possess luteolytic activity.

2. Description of the Conventional Art

Muchowski et al., U.S. Pat. No. 3,985,791, describe the invention of 16-phenoxy and 16-(o, m, or p)-substituted phenoxy derivatives of 9α,11α,15α-trihydroxy-17,18,19,20-tetranorprosta-4,5,13-trans-trienoic acids and multistep process for the production of these compounds. Their approach to the fenprostalene (formula II, Z=α-hydroxyl) involves an intermediate compound of the general formula I, wherein $R^1$ and $R^2$ are acetyl and P is methoxycarbonylethyl by using somewhat expensive 4-pentynoic acid and an excessive amount of explosive diazomethane. They introduced an allenyl group in fenprostalene from this intermediate by the reaction with lithium dimethycuprate. The specific formation of protonated allene from propargylic ester is sensitive to various factors depending on the kind of propargylic derivatives, cuprate reagents, reaction temperature, work-up conditions, etc. (P. Crable et al., Tetrahedrom Lett., 1975, 4615; C. Sahlberg et al, Acta. Chem. Scand., 1982, B 36, 179). In addition, the process of U.S. Pat. No. 3,985,791 requires accurate control in order to avoid the formation of undesirable alkylated allene isomers and alkylated acetylene isomers which may be formed by the introduction of protonated allenes (P. Crable et al., Tetrahedron, 1979, 35, 2931; A. Claesson et al., Tetrahedron Lett., 1975, 1509; A. Alexakis et al., J. Am Chem. Soc., 1990, 112, 8042; T. L. MacDonald et al., J. Org. Chem., 1980, 45, 4740).

Van Horn et al. (U.S. Pat. No. 4,178,457) disclose enprostil and a process for manufacturing thereof. Van Hom's process is a three step process consisting of protecting 11α and 15 hydroxyl groups of the compounds of U.S. Pat. No. 3,985,791, selective oxidation of 9-hydroxyl group to 9-keto group and removal of protecting groups.

Cooper et al. (U.S. Pat. No. 4,600,785) describes a multistep process for the synthesis of enprostil using an intermediate compound in formula I, wherein $R^1$ is t-butyldimethylsilyl, $R^2$ is hydrogen, and P is hydrogen. They prepared the intermediate compound via a 6-step sequence starting from 1α-hydroxy-4α-(tetrahydropyran-2-yloxy)-3β-(3α-(tetrahydropyran-2-yloxy)-4-phenoxy-1(E)-buten-1-yl)-cyclopent-2α-yl)aceticacid lactone consisting of hydrolysis of the lactone ring, esterification of the acid to methyl ester, protection of the 9-hydroxyl group, reduction of methyl ester, oxidation of the resulting alcohol to aldehyde, and addition of an ethynyl group. They introduced an allenyl group in enprostil from this intermediate I by Claisen rearrangement and one-carbon elongation via a multistep process. Their approach requires a lengthy reaction due to the need to selectively functionalize the C-6 and C-9 hydroxyl groups (PG numbering) and one-carbon elongation.

SUMMARY OF THE INVENTION

The object of the present invention is to provide intermediates useful for the synthesis of 16-phenoxy-prostatrienoic acid derivatives which is more efficient and make the process of producing 16-phenoxy-prostatrienoic acid derivatives such as enprostil and fenprostalene easy.

Another object of the present invention is to provide a preparing method of the intermediate useful for the synthesis of 16-phenoxy-prostatrienoic acid derivatives by using inexpensive metal acetylide and introducing an allenyl group conveniently without accompanying alkylated allene or alkylated acetylene. Besides, the preparing method of the present invention precludes the need to selectively functionalize the C-6 and C-9 hydroxyl groups (PG numbering) and one-carbon elongation.

DETAILED DESCRIPTION OF THE INVENTION

The invention encompasses compounds of formula I, VIII, IX, XI, and XII which are novel intermediates for producing 16-phenoxyprostatrienoic acid derivatives II.

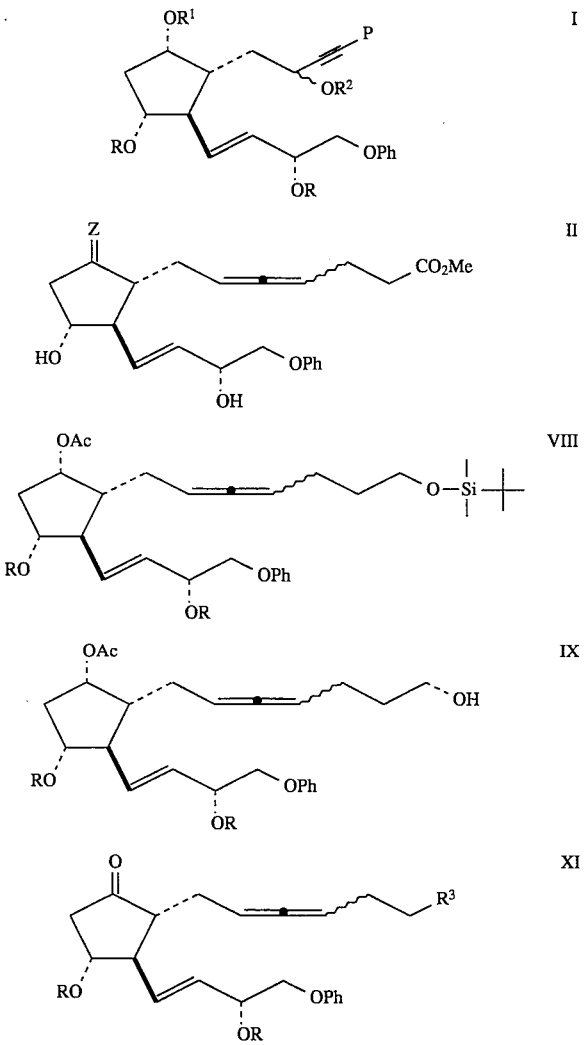

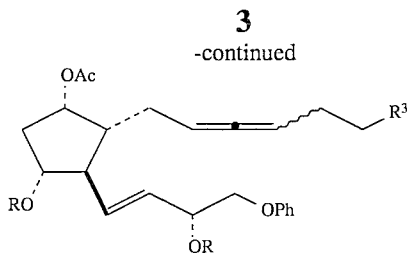

The numbering system assigned to the prostanoic acid skeleton is as follows:

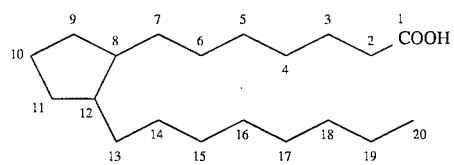

The intermediate compounds I according to the present invention are those compounds having the formula (I)

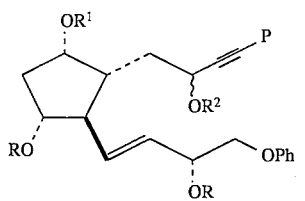

wherein R is tetrahydropyranyl, tetrahydrofuranyl, 2-ethoxyethyl, 3-t-butyldimethylsilyl triisopropylsilyl or triethylsilyl group; $R^1$ and $R^2$ are independently hydrogen or ester-forming group such as acetyl; P is hydrogen, trimethylsilyl or tri-n-butyltin; wavy line indicates an epi-stereoisomeric mixture.

When $R^1$ and/or $R^2$ are hydrogen, the hydrogen can be substituted with ester group by esterification of the compound (I). Preferably, the hydrogen can be substituted with an acetyl group by treatment of the compound (I) with acetic anhydride or acetyl chloride, triethylamine, and catalytic amount of 4-dimethylaminopyridine in methylene chloride. When P is trimethylsilyl or tri-n-butyltin, such protection groups can be removed by reaction with tetraabutylmmonium fluoride or n-butyllithium.

The intermediate compounds (I) according to the present invention comprising can be obtained by reaction of the lactol compound (V) with metal acetylide reagent represented as formula VI as indicated the following Scheme 1.

Scheme 1

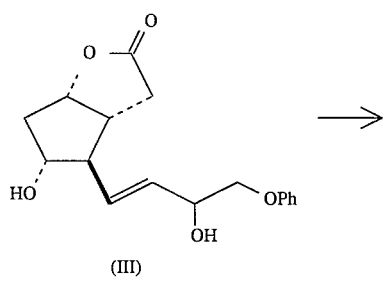

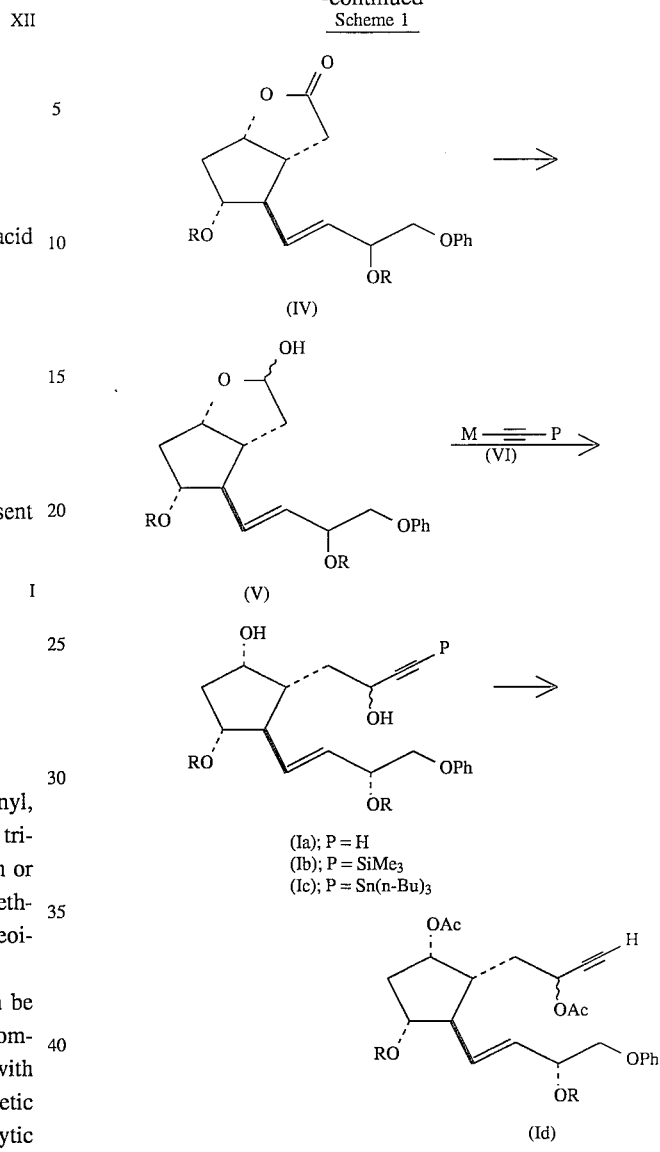

In the above general compounds, R, $R^1$, $R^2$, P and the wavy line have the same meaning as defined in the foregoing, and M is lithium, chloromagnesium, or bromomagnesium.

The detailed description of the invention is as follows:

The known dihydroxy compound III is converted to lactone compound IV by etherification. The lactone compound IV is converted to the known lactol compound V. The lactol compound V is used as the starting compound in the present invention. The novel intermediate compound I can be obtained from the lactol compound V via ring opening reaction by metal acetylide reagent compound VI.

A preparing method for the intermediate compound I of the present invention is illustrated in more detailed as follows:

The lactol compound V, which is the starting material of the invention, can be prepared by a known method described in U.S. Pat. No. 3,985,791 and J. Med. Chem., 24, 1353 (1984). The dihydroxyl compound III is convened to the known lactone compounds IV by etherification; wherein R represents an ether forming group such as tetrahydropyranyl, tetrahydrofuranyl, 2-ethoxyethyl, 3-t-butyldimethylsilyl triisopropylsilyl or triethylsilyl group.

The lactone compound IV is converted to the lactol compound V by treatment of 1.1 equivalent of diisobutylaluminum hydride in an aprotic solvent such as toluene or tetrahydrofuran, at reduced temperature between −40°—−78° C. The resulting reaction mixture is quenched with methanol and brine and allowed to come to 15°–25° C. and vigorously stirred. The resulting precipitate is removed by filtration and washed with diethyl ether several times. The combined filtrate is dried over anhydrous magnesium sulfate and evaporated to form the lactol compound V.

The present compound I can be prepared by any number of appropriate methods, and some examples of the preparation are as below.

First, the 5–20 equivalents, preferably 10 equivalents of acetylene compound VI, wherein M is lithium and P is trimethylsilyl, is added to a solution of the compound V in tetrahydrofuran at −78° C. After 10 min. the reaction mixture is allowed to come to 20°–25° C. to form the compound Ib. The compound Ib is obtained as an epimeric mixture at C-6 (PC numbering) and provided a degree of separation on thin-layer chromatography (ethyl acetate/hexane=2:1). Diastereomerically pure 16-phenoxy-prostatrienoic acid derivatives II can be prepared by the silica gel column chromatographic separation of an epimeric mixture of Ib. The crude epimeric mixture of Ib is desilylated to form Ia, wherein $R^1$ and $R^2$ are hydrogen and P is hydrogen, by treating 1.2 equivalent of tetra-n-butylammonium fluoride (TBAF) in tetrahydrofuran at 20°–25° C. The acetylene compound VI, wherein M is lithium and P is trimethylsilyl, is prepared from trimethylsilylacetylene by treating 1 equivalent of n-butyllithium in tetrahydrofuran at −78° C. with stirring for 10 minutes.

The alternative method for the preparation of Ia, wherein $R^1$ and $R^2$ are hydrogen and P is hydrogen, is the reaction of the lactol compound V with lithium tri-n-butylstannanylacetylide of the formula VI, wherein M is lithium and P is tri-n-butyltin. The 5–20 equivalents, preferably 10 equivalents of acetylene compound VI, wherein M is lithium and P is tributyltin, is added to a solution of the compound V in tetrahydrofuran at −78° C. After 10 min. the reaction mixture is allowed to come to 20°–25° C. to form the compound Ic. The tri-n-butyltin group of Ic is removed to form the compound Ia by treating the solution of crude Ic in tetrahydrofuran with 1 equivalent of n-butyllithium.

Another alternative method for the preparation of Ia, wherein $R^1$ and $R^2$ are hydrogen and P is hydrogen, is the reaction of the lactol compound V with lithium acetylide of the formula VI, wherein M is lithium and P is hydrogen. The 5–20 equivalents, preferably 10 equivalents of lithium acetylide is added to a solution of the compound V in tetrahydrofuran at −78° C. After 10 min. the reaction mixture is allowed to come to 20°–25° C. to form the compound Ia.

Another alternative method for the preparation of Ia, wherein $R^1$ and $R^2$ are hydrogen and P is hydrogen, is the reaction of the lactol compound V with lithium tri-n-butylstannanylacetylide of the formula VI, wherein M is lithium and P is tri-n-butyltin. The 5–20 equivalents, preferably 10 equivalents of acetylene compound VI, wherein M is lithium and P is tributyltin, is added to a solution of the compound V in tetrahydrofuran at −78° C. After 10 min. the reaction mixture is allowed to come to 20°–25° C to form the compound Ic. The tri-n-butyltin group of Ic is removed to form the compound Ia by treating the solution off crude Ic in tetrahydrofuran with 1 equivalent of n-butyllithium.

Another alternative method for the preparation of Ia, wherein $R^1$ and $R^2$ are hydrogen and P is hydrogen, is the reaction of the lactol compound V with lithium acetylide of the formula VI, wherein M is lithium and P is hydrogen. The 5–20 equivalents, preferably 10 equivalents of lithium acetylide is added to a solution of the compound V in tetrahydrofuran at −78° C. After 10 min. the reaction mixture is allowed to come to 20°–25° C. to form the compound Ia.

Another alternative method for the preparation of Ia, wherein $R^1$ and $R^2$ are hydrogen and P is hydrogen, is the reaction of the reaction of the lactol compound V with ethynylmagnesium halide of the formula VI, wherein M is bromomagnesium or chloromagnesium and P is hydrogen. The 5–20 equivalents, preferably 10 equivalents of ethynylmagnesium halide is added to a solution of the compound V in tetrahydrofuran at 5°–25° C. After 4 hours, the reaction is completed to form the compound Ia.

The method to form the intermediate compound Ia is more preferable since other methods such as method for preparing Ic or Id necessitate additional deprotecting process. On the other hand, the first method using trimethylsilylacetylene is useful for the preparation of diastereomerically pure 16-phenoxy-prostatrienoic acid derivatives.

The compound Ia is Convened to the diacetyl compound Id by treatment of acetyl chloride, preferably acetic anhydride in the presence of a catalytic mount of 4-dimethylaminopyridine in chlorinated hydrocarbon solvent such as dichloromethane or chloroform, at 15°–25° C. The acetylation reaction is carried out in the presence of amine base such as triethylamine, diisopropylethylamine, pyridine, 2,6-lutidine, 3,5-lutidine, 2,4,6-colidine or dicyclohexyethylamine.

Accordingly, the overall reaction process is simplified since the present invention need not differentiate two hydroxy groups in the compound Ia.

A preparing method for prostatrienoic acid derivatives from the compound I according to the present invention is illustrated in Scheme 2.

Scheme 2

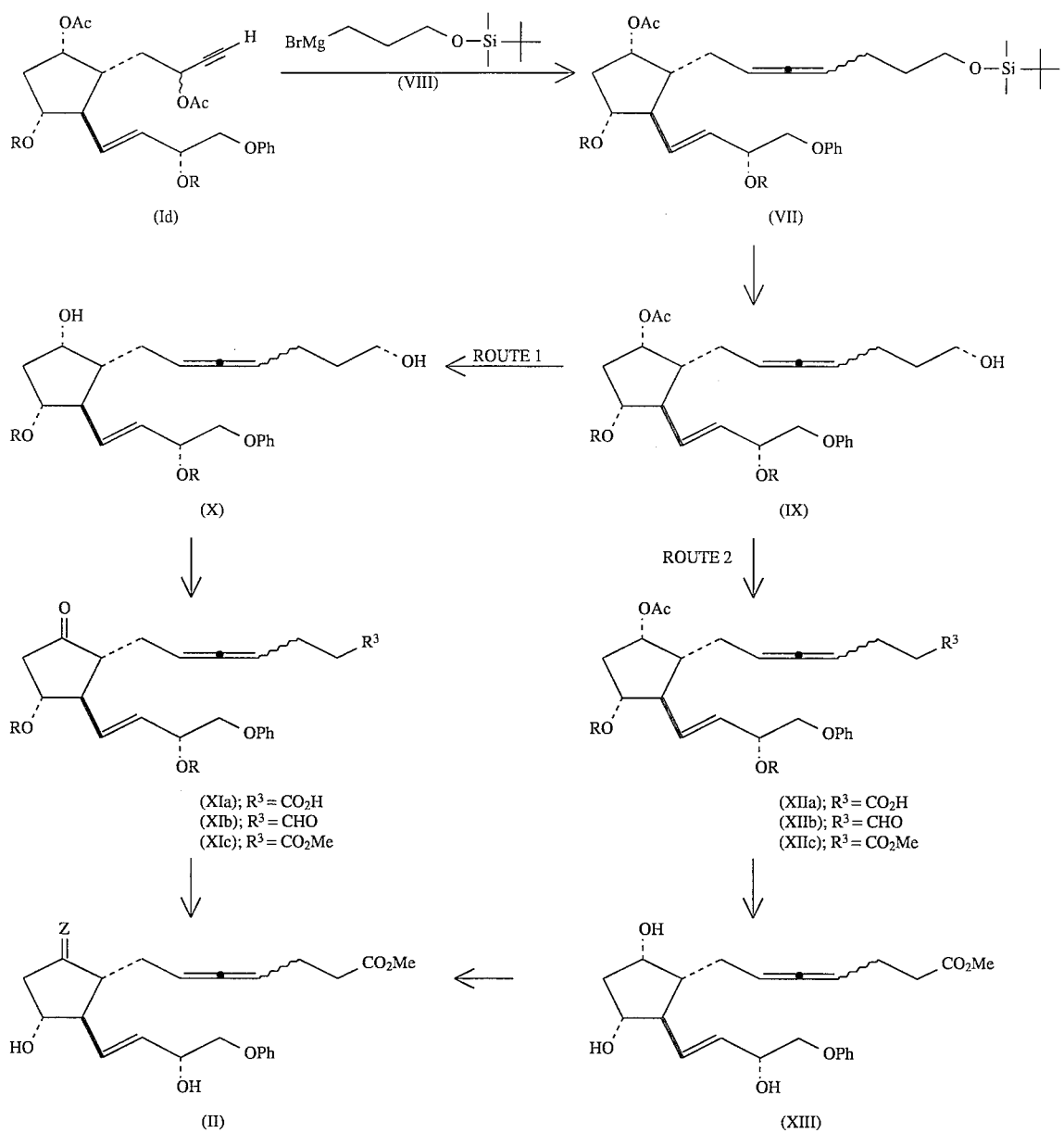

The intermediate compound I, wherein $R^1$ and $R^2$ are acetyl and P is hydrogen, is converted to the compound VIII by the reaction with Grignard reagent VII. The compound VIII is desilylated to the compound IX by treatment of tetra-n-butylammonium fluoride. The compound IX is transferred to the prostatrienoic acid derivatives II by two routes as shown in Scheme 2. In route 1, the compound IX is deacetylated to form the compound X by treatment of methanolic potassium carbonate. The compound X is oxidized and then deprotected to form 16-phenoxyprostatrienoic acid derivative II, wherein Z is oxygen.

In route 2, the compound IX is oxidized first and then deprotected to form 16-phenoxyprostatrienoic acid derivative II, wherein Z is α-hydroxyl.

The diacetyl compound Id is converted to the allene compound VIII by treating a solution of 3-t-butyldimethylsilyloxypropylmagnesium bromide in tetrahydrofuran in the presence of a catalytic amount of copper iodide triethylphosphite complex. The preparation of allene compounds by the reaction of propargyl ether or propargyl ester with Grignard reagent in the presence of a catalytic amount of copper reagent is disclosed in C. Sahlberg et al., Acta. Chem. Scand., 1982, B 36, 179 and A. Alexakis et al., J. Am. Chem. Soc., 1990, 112, 8042. But, the application of the allene formation to the synthesis of prostaglandins with allenyl side chain is rare.

The solution of 3-t-butyldimethylsilyloxypropyl-magnesium bromide in tetrahydrofuran in the presence of 0.1–0.2 mol equivalent of copper iodide triethylphosphite complex (CuI.P(OEt)$_3$) is added dropwise to the solution of diacetyl compound Id in tetrahydrofuran at −40°–0° C. to form the allene compound VIII. The reaction mixture is allowed to come to 20°–25° C. stirred for 2 hrs. If the reaction is not completed, additional 1–10 equivalents of Grignard reagent is added or unreacted starting material can be recovered by silica gel column chromatography without decomposition. The condition of the allene-forming reaction is not difficult and proceeds cleanly since the reaction does not accompany undesirable product such as alkylated acetylene or protonated allene compound as described in P. Crable et al., Tetrahedron, 1979, 35, 2931.

The compound VIII is desilylated to form the compound IX by treating tetra-n-butylammonium fluoride in tetrahydrofuran and stirring at 15°–25° C. for 4 hrs.

The compound IX is converted to the 16-phenoxyprostatrienoic acid derivatives II, wherein Z is oxygen, or α-hydroxyl by way of two routes in Scheme 2.

The reaction route 1 describes the formation of 16-phenoxyprostatrienoic acid derivatives II, wherein Z is oxygen starting from the intermediate compound IX. The detailed description of the reaction route 1 is as follows:

The compound IX is deacetylated to form the compound X by treating 1.2–2 equivalents of anhydrous potassium carbonate in methanol and stirring at 15°–25° C. for 5 hours.

The dihydroxy compound X is convened to the 9-oxo compound XIa by treating Jones reagent in acetone or pyridinium dichromate in N,N-dimethylformamide. Treatment of the compound X with 3.5–5 equivalents of Jones reagent at −30°–20° C. in acetone and stirring for 1 hour complete the Jones oxidation reaction to form 9-oxo compound XIa.

Alternatively, treatment of the compound X with 5–10 equivalents of pyridinium dichromate at 15°–25° C. in N,N-dimethylformamide and stirring for 1–3 days also produces 9-oxo compound XIa.

The 9-oxo compound XIa is convened to the methyl ester compound XIc by treating excess diazomethane in diethyl ether. The use of diazomethane has some disadvantage in large-scale processes since diazomethane is explosive. In the present invention, the methyl ester compound XIc is obtained by consecutive oxidation without using explosive diazomethane. The dihydroxy compound X is treated with 5–10 equivalents of pyridinium dichromate in methylene chloride for 12–24 hours. The reaction mixture is diluted with diethyl ether and filtered through Celite-545 to remove insoluble material. The filtrate is evaporated to form the aldehyde compound XIb. The crude aldehyde compound XIb is dissolved again in N,N-dimethylformamide and methanol followed by treating 5–10 equivalents of pyridinium dichromate. After 12–24 hours, the mixture is diluted with diethyl ether and filtered through Celite-545 to remove insoluble material. The filtrate is evaporated to form the ester compound XIc. The ester compound XIc is deprotected to form the prostatrienoic acid derivative II (enprostil, Z=oxygen) by treating mixed solvent such as formic acid/$H_2O$/tetrahydrofuran or acetic acid/$H_2O$/tetrahydrofuran at 20°–30° C. for 12–72 hours.

Alternatively, the compound IX is convened to the 16-phenoxyprostatrienoic acid derivatives II (fenprostalene, Z=α-hydroxyl) by way of route 2 in Scheme 2.

The reaction mute 2 describes the formation of 16-phenoxyprostatrienoic acid derivatives II (fenprostalene) starting from the intermediate compound IX. The detailed description of the reaction route 2 is as follows: The intermediate compound IX is convened to the di-ester compound XIIc through the aldehyde compound XIIb by the same procedure as for the formation of the compound XIc from the compound X.

The di-ester compound XIIc is treated with 2–4 equivalents of anhydrous potassium carbonate in methanol and stirred at 15°–25° C. for 24 hours. After cooling to 0° C., the mixture is neutralized carefully with aqueous 1N hydrochloric acid solution and treated with water and diethylether. The organic phase is separated, dried over anhydrous magnesium sulfate, and evaporated to form the compound XIII.

Finally, the ester compound XIII is deprotected to form the prostatrienoic acid derivative II (fenprostalene, Z=α-hydroxyl) by the same procedure as for the formation of the compound II (enprostil) from the compound XIc.

These examples are given by way of illustration only and are not constructed as limiting the practice of this invention.

EXAMPLE 1

[1α-Hydroxy-4α-(tetrahydropyran-2-yloxy)-3β-(3α-(tetrahydropyran-2-yloxy)-4-phenoxy-1(E)-buten-1-yl)-cyclopent-2α-yl)]-1-but-3-yn-2-ol (Ia)

To a solution of 1α-hydroxy-4α-(tetrahydropyran-2-yloxy)-3β-(3α-(tetrahydropyran-2-yloxy)4-phenoxy- 1(E)-buten-1-yl)-cyclopent-2α-yl) acetaldehyde lactol V (103 mg,: 0.2 mmol) in THF (0.6 ml), was added a solution of ethynyl-magnesium bromide (2.65 ml, 0.5M solution in THF) dropwise at 0° C. The reaction was allowed to reach room temperature and further stirred for 5 hours. After cooling to 0° C. the mixture was treated with saturated aqueous $NH_4Cl$ (1 ml) and partitioned with diethyl ether (20 ml) and water (10 ml). The ether solution was washed with saturated aqueous NaCl, dried ($MgSO_4$) and evaporated. The residue was purified by flash column chromatography to afford the title compound (Ia, 99 mg, 91%): IR (neat) 3294, 2936, 2870, 1497, 1454 $cm^{-1}$, $^1$H NMR δ 6.87–7.32 (m, 5 H), 5.46–5.85 (m, 2 H), 4.42–5.00 (m, 4 H), 3.70–4.39 (m, 6 H), 3.42–3.57 (m, 2 H), 2.42–2.50 (m, 1 H).

EXAMPLE 2

[1α-Hydroxy-4α-(tetrahydropyran-2-yloxy)-3β-(3α-(tetrahydropyran-2-yloxy)-4-phenoxy- 1(E)-buten-1-yl)-cyclopent-2α-yl)]-1-but-3-yn-2-ol (Ia)

To a solution of THF (5 ml), was bubbled purified acetylene gas (ca. 120 ml) through long needle with stirring at −78° C. over 10 minutes. To this, n-BuLi (1.6M, 2.60 ml) was added and stirred for 20 minutes. To the resulting lithium acetylide solution, a solution of above lactol V (197 mg, 0.41 mmol) in THF (2 ml) was added. The reaction mixture was warmed to room temperature over 30 min. and further stirred for 2 h. After cooling to 0° C. the mixture was treated with saturated aqueous $NH_4Cl$ (10 ml) and partitioned with diethyl ether (20 ml) and water (10 ml). The ether solution was washed with saturated aqueous NaCl, dried ($MgSO_4$) and evaporated. The residue was concentrated and purified by flash column chromatography to afford the compound Ia (170 mg, 82%).

EXAMPLE 3

[1α-Hydroxy-4≠-(tetrahydropyran-2-yloxy)-3β-(3α-(tetrahydropyran-2-yloxy)-4-phenoxy-1(E)-buten-1-yl)-cyclopent-2α-yl)]-1-but-3-yn-2-ol (Ia)

To a solution of ethynyl-tri-n-butyltin (1.06 g, 3.37 mmol) in THF (5 ml), n-BuLi (1.6M, 2.2 ml) was added dropwise at −78° C. and stirred for 20 min. To the resulting lithium anion solution, a solution of the lactol V (160 mg, 0.33 mmol) in THF (1 ml) was added. The reaction mixture was warmed to room temperature and further stirred for 2 hrs. After cooling to 0° C the mixture was treated with saturated aqueous $NH_4Cl$ (10 ml) and partitioned with diethyl ether (20 ml) and water (10 ml). The ether solution was washed with saturated aqueous NaCl, dried (MgSO$_4$) and evaporated. The residue was short column chromatographed to remove tetra-n-butyltin and unreacted ethynyl-tri-butyltin (hexane to ethyl acetate). The ethyl acetate fraction was concentrated to afford the compound Ic, which was directly dissolved in THF (3 ml), and treated with n-BuLi (1.6M, 0.7 ml) dropwise at −78° C. The mixture was warmed to 25° C. for 10 min and cooled to 0° C. The mixture was treated with saturated aqueous NH$_4$Cl (1 ml) and partitioned with diethyl ether and water. The ether solution was washed with saturated aqueous NaCl, dried (MgSO$_4$) and evaporated. The residue was purified by flash column chromatography (50% petrolum ether in ethyl acetate) to afford the compound Ia (138 mg, 82%) as an oil.

EXAMPLE 4

[1 α-Hydroxy-4α-(tetrahydropyran-2-yloxy)-3β-(3α-(tetrahydropyran-2-yloxy)-4-phenoxy-1(E)-buten-1-yl)-cyclopent-2α-yl)]-1-but-3-yn-2-ol (Ia)

To a solution of trimethylsilylacetylene (217 mg, 2.2 mmol) in THF (5 ml), n-BuLi (1.6M, 1.38 ml) was added dropwise at −78° C. and stirred for 20 minutes. To the resulting lithium anion solution, a solution of above lactol V (150 mg, 0.31 mmol) in THF (1 ml) was added. The reaction mixture was warmed to room temperature and further stirred for 2 hours. After cooling to 0° C. the mixture was treated with saturated aqueous NH$_4$Cl (10 ml) and partitioned with diethyl ether (20 ml) and water (10 ml). The ether solution was washed with saturated aqueous NaCl, dried (MgSO$_4$) and evaporated to afford the compound Ib as an epimeric mixture at C-6 (PC numbering) from the thin-layer chromatography (ethyl acetate/hexane-2:1). The compound Ib was dissolved in THF (1 ml) without further separation as a pure epimer, and treated with TBAF (1.0M in THF, 0.37 ml) at room temperature for 2 hours. The mixture was concentrated and purified by flash column chromatography to afford the compound Ia (148 mg, 93%).

EXAMPLE 5

2αβ-Acetoxy-[(1α-acetoxy-4α-(tetrahydropyran-2-yloxy)-3β-(3α-(tetrahydropyran-2-yloxy)-4-phenoxy-1(E)-buten-1-yl)-cyclopent-2α-yl)]-1-but-3-yne (Id)

A solution of [1α-hydroxy-4α-(tetrahydropyran-2-yloxy)-3β-(3α-(tetrahydro-pyran-2-yloxy)-4-phenoxy-1(E)-buten-1-yl)-cyclopent-2α-yl)]-1-but-3-yn-2-ol (Ia) (99 mg, 0.119 mmol), triethylamine (139 mg, 1.37 mol), acetic anhydride (139 mg, 1.32 mmol) and a catalytic amount of DMAP in dichloromethane (2 ml) was stirred at room temperature for 3 hours. The mixture was concentrated and purified by flash column chromatography (20% ethyl acetate in hexane) to afford the compound Id (106 mg, 91%) as an oil: IR(neat) 2936, 2859, 1742, 1601, 1244 cm$^{-1}$ $^1$H NMR δ 6.86–7.40 (m, 5 H), 5.58–5.85 (m, 2 H), 5.10–5.48 (m, 2 H), 4.50–5.00 (m,3 H), 3.77–4.20 (m, 5 H), 3.41–3.55 (m, 2 H), 2.37–2.46 (m, 1 H), 2.02, 2.05, 2.06 and 2.07 (four s, 6 H), 1.95–2.15 (m, 6 H).

EXAMPLE 6

[1α-Acetoxy-4α-(tetrahydropyran-2-yloxy)-3β-(2α-(tetrahydropyran-2-yloxy)-4-phenoxy-1(E)-buten-1-yl)-cyclopent-2α-yl)]-7-t-butyldimethylsilyloxy-1-hepta-2,3-diene (VIII)

A solution of 3-t-butyldimethylsilyloxypropylmagnesium bromide (prepared from 3-t-butyldimethylsilyloxypropyl bromide (0.5 g, 1.98 mmol) and magnesium (72 mg, 2.96 mg atom) in THF (10 ml)) was added dropwise to a solution of 2α,β-acetoxy-[(1α-acetoxy-4α-(tetrahydropyran-2-yloxy)-3β-(2α-(tetrahydropyran-2-yloxy)-4-phenoxy-1(E)-buten-1-yl)-cyclopent-2α-yl)]-1-but-3-yne (Id) (102 mg, 0.17 mmol) and CuI.P(OEt)$_3$ (62 mg, 0.174 mmol) in THF (5 mL) at −40° C. for 5 minutes. The mixture was allowed to warm to 0° C. and further stirred for 2 hours. The mixture was treated with a mixture of aqueous NH$_3$ (2 parts) and saturated aqueous NH$_4$Cl (10 ml). The aqueous phase was washed with diethyl ether (20 ml×2), and the combined organic phase was washed with a mixture of aqueous NH$_3$/NH$_4$Cl (10 ml×2) and then dried (MgSO$_4$) and concentrated. The residue was purified by flash column chromatography (15% ethyl acetate in pet. ether) to afford the title compound VIII (92 mg, 76%) as an oil: IR (neat) 2944, 2853, 1962, 1738, 1599, 1375 cm$^{-1}$ $^1$H NMR δ 6.88–7.53 (m, 5 H), 5.50–5.82 (m, 2 H), 4.86–5.25 (m, 3 H), 4.48–4.83 (m, 3 H), 3.32–4.18 (m, 9 H), 2.07 and 2.08 (two s, 3 H), 0.86 (s, 9 H).

EXAMPLE 7

[1α-Acetoxy-4α-(tetrahydropyran-2-yloxy)-3β-(3α-(tetrahydropyran-2-yloxy)-4-phenoxy-1(E)-buten-1-yl)-cyclopent-2α-yl)]-7-hepta-4,5-diene-1-ol (IX)

To a solution of [1α-acetoxy-4α-(tetrahydropyran-2-yloxy)-3β-(3 α-(tetrahydro-pyran-2-yloxy)-4-phenoxy-1(E)-buten-1-yl)-cyclopent-2α-yl)]-7-t-butyl-dimethylsilyloxy-1-hepta-2,3-diene (VIII) (63 mg, 0.09 mmol) in THF (0.5 ml), a solution of TBAF (108 μl, 0.108 mmol, 1M solution in THF) was added and stirred at room temperature for 3 hours. The mixture was evaporated and purified by flash column chromatography (50% ethyl acetate in hexane) to afford the title compound (IX) (52 mg, 99%): IR (neat) 3233, 2940, 2870, 1962, 1736, 1599, 1246 cm$^{-1}$ $^1$H NMR δ 6.86–7.31 (m, 5 H), 5.55–5.72 (m, 2 H), 5.03–5.15 (m, 3 H), 4.49–4.63 (m, 3 H), 3.79–4.11 (m, 5 H), 3.60–3.68 (m, 2 H), 3.45–3.52 (m, 2 H), 2.04 (s, 3 H).

EXAMPLE 8

[1α-Hydroxy-4α-(tetrahydropyran-2-yloxy)-3β-(3α-(tetrahydropyran-2-yloxy)-4-phenoxy-1(E)-buten-1-yl)-cyclopent-2α-yl)]-7 -hepta-4,5-diene-1-ol (X)

A solution of [1α-acetoxy-4α-(tetrahydropyran-2-yloxy)-3β-(3α-(tetrahydro-pyran-2-yloxy)-4-phenoxy-1(E)-buten-1-yl)-cyclopent-2α-yl)]-7-hepta-4,5-diene-1-ol (IX) (52 mg, 0.09 mmol) in methanol (0.5 ml) was treated with anhydrous potassium carbonate (14 mg, 0.107 mmol) and stirred for 5 hours. The mixture was concentrated and purified by flash column chromatography (67% ethyl acetate in hexane) to afford the title compound (X) (48 mg, 98%) as an oil: IR (neat) 3440, 2932, 2871, 1961, 1597, 1449, 1385, 1346, 1246, 1203, 1129, 1073, 977 cm$^{-1}$ $^1$H NMR δ 6.88–7.30 (m, 5 H), 5.47–5.77 (m, 2 H), 4.93–5.19 (m, 2 H), 4.66–4.80 (m, 2 H), 4.56–4.58 (m, 1 H), 3.84–4.24 (m, 6 H), 3.61–3.77 (m, 2 H), 3.43–3.52 (m, 2 H)

EXAMPLE 9

Methyl-9-oxo-11α,15α-bis-(tetrahydropyran-2-yloxy)-16-phenoxy-17,18,19,20-tetranor-prosta-4,5,13(E)-trienoate (XIc)

To a solution of [1α-hydroxy-4α-(tetrahydropyran-2-yloxy)-3β-(3α-(tetrahydro-pyran-2-yloxy)-4-phenoxy-1(E)-buten-1-yl)-cyclopent-2α-yl)]-7-hepta-4,5-diene-1-ol (X) (26 mg, 0.048 mmol) in dichloromethane (1 ml), pyridinium dichromate (PDC, 72 mg, 0.191 mmol) was added and stirred for 24 hours. The mixture was diluted with diethyl ether (10 ml) and the resulting precipitate was filtered through Florisil and washed several times with diethyl ether.

The combined organic solution was concentrated to afford a crude aldehyde compound XIb. The aldehyde compound XIb was dissolved in methanol (50 μl) and DMF (300 μl) and treated with PDC (100 mg, 0.265 mmol). After stirring for 24 hours the mixture was diluted with diethyl ether (10 ml) and the resulting precipitate was filtered through Florisil and washed several times with diethyl ether. The combined organic solution was dried (MgSO$_4$) and concentrated to afford the title compound (XIc) (15 mg, 55%) as an oil: IR 2924, 2855, 1965, 1741, 1597, 1495 cm$^{-1}$ $^1$H NMR δ 6.87–7.27 (m, 5 H), 5.53–5.80 (m, 2 H), 4.93–5.18(m, 2 H), 4.69–4.82 (m,2 H), 4.52–4.58 (m, 1 H), 3.82–4.24 (m, 5 H), 3.66 (s, 3 H).

EXAMPLE 10

Methyl 9-oxo-11α,15α-dihydroxy-16-phenoxy-17,18,19,20-tetranorprosta-4,5,13(E)-trienoate (II, Z=oxygen, Enprostil)

A solution of methyl 9-oxo-11α,15α-bis-(tetrahydropyran-2-yloxy)- 16-phenoxy-17,18,19,20-tetranorprosta-4,5,13(E)-trienoate (XIc) (21 mg, 0.037 mmol) in formic acid (19 mL), water (11 mL), and THF (3 mL) was stirred at 40° C for 14 hours. The mixture was concentrated in vacuo. and purified by flash column chromatography (50% ethyl acetate in hexane) to afford the title compound (II, Z–oxygen, enprostil, 10 mg, 67%) as an oil: IR(neat) 3300, 2925, 2857, 1963, 1740, 1596, 1494, 1455 cm$^{-1}$ $^1$H NMR δ 6.91–7.33 (m, 5 H), 5.79–5.83 (m, 2 H), 5.07–5.14 (m, 2 H), 4.57–4.60 (m, 1 H), 3.92–4.20 (m, 3 H), 3.66 (s, 3 H); $^{13}$C NMR δ 213.40, 213.61 (C$_9$), 204.72, 204.80 (C$_5$), 173.54 (C$_1$), 158.39 (C$_{17}$), 132.98, 133.07 (C$_{14}$), 131.94 (C$_{13}$), 129.59, 129.68 (C$_{19}$), 121.3 121.49 (C$_{20}$), 114.51, 114.60 (C$_{18}$), 90.20, 90.27 (C$_4$), 88.74 (C$_6$), 71.83, 72.01 (C$_{11}$), 71.62 (C$_{16}$), 70.76 (C$_{15}$), 54.15, 54.20 (C$_{12}$), 53.28, 53.42 (C$_8$), 51.64, 51.67 (OCH$_3$), 46.06 (C$_{10}$), 33.11, 33.26 (C$_2$), 26.76(C$_7$), 23.74, 23.85 (C$_3$); MS (EI, 60 eV) 382 (M$^+$–H$_2$O), 275, 221, 195, 169, 145, 131,115, 91, 77 (base peak), 65, 39.

EXAMPLE 11

Methyl-9α-acetoxy-11α,15α-bis-(tetrahydropyran-2-yloxy)-16-phenoxy-17, 18, 19,20-tetranorprosta-4,5, 13(E)-trienoate (XIIc)

To a solution of [1α-acetoxy-4α-(tetrahydropyran-2-yloxy)-3β-(3α-(tetrahydro-pyran-2-yloxy)-4-phenoxy 1(E)-buten-1-yl)-cyclopent-2α-yl)]-7-hepta-4,5-diene-1-ol (IX) (17 mg, 0.03 mmol) in dichloromethane (1 ml) was added pyridinium dichromate (PDC, 22 mg, 0.06 mmol) and stirred for 20 hours. The mixture was diluted with diethyl ether (10 ml) and the resulting precipitate was filtered through Florisil and washed several times with diethyl ether. The combined organic solution was concentrated to afford a crude aldehyde compound XIIb. The compound XIIb was dissolved in methanol (50 μl) and DMF (300 μl) and treated with PDC (57 mg, 0.15 mmol). After stirring for 20 hours the mixture was diluted with diethyl ether (10 ml) and the resulting precipitate was filtered through Florisil and washed several times with diethyl ether. The combined organic solution was dried (MgSO$_4$) and concentrated to afford the title compound (XIIc) (15 mg, 84%) as an oil: IR 2936, 2859, 1962, 1738, 1626, 1497, 1246 cm$^{-1}$ $^1$H NMR δ 6.88–7.30 (m, 5 H), 5.58–5.72(m, 2 H), 4.93–5.14(m, 2 H), 4.50–4.83 (m, 3 H), 3.82–4.24 (m, 5 H), 3.66 (s, 3 H), 3.43–3.52 (m, 2 H).

EXAMPLE 12

Methyl-9α-hydroxy-11α,15α-bis(tetrahydropyran-2-yloxy)-16-phenoxy-17,18,19,20-tetranorprosta-4,5, 13(E)-trienoate (XIII)

To a solution of methyl 9α-acetoxy-11α,15α-bis-(tetrahydropyran-2-yloxy)-16-phenoxy-17,18,19,20-tetranorprosta-4,5,13(E)-trienoate (XIIc) (12 mg, 0.02 mmol) in absolute methanol (1 ml), anhydrous potassium carbonate (5 mg, 0.04 mmol) was added and stirred at room temperature for 14 hours. The reaction mixture was cooled to 0° C. and neutralized carefully with aqueous 1N HCl solution. The mixture was partitioned with ether (10 ml) and water (10 ml). The aqueous solution was extracted with ether (10 ml) and the combined ether solution was dried (MgSO$_4$) and concentrated to afford the title compound (XIII) (10 mg, 89%) as an oil: IR 3449, 2936, 1961, 1736, 1595, 1439 cm$^{-1}$ $^1$H NMR δ 6.90–7.32 (m, 5 H), 5.53–5.75 (m, 2 H), 4.95–5.18 (m, 3 H), 4.68–4.70 (m, 1 H), 3.81–4.26 (m, 6 H), 3.67 (s, 3 H).

EXAMPLE 13

Methyl-9α-hydroxy-11α,15α-dihydroxy-16-phenoxy-17,18,19,20-tetranorprosta-4,5,13(E)-trienoate(II, Z=α-hydroxyl, fenprostalene)

A solution of methyl 9α-hydroxy-11α-15α-bis-(tetrahydropyran-2-yloxy)-16-phenoxy-17,18,19,20-tetranorprosta-4,5,13(E)-trienoate (XIII) (10 mg, 0.017 mmol) in formic acid (9.5 ml), water (5.5 ml), and THF (1.5 ml) was stirred at 40° C. for 20 hours. The mixture was concentrated in vacuo. and purified by flash column chromatography (50% ethyl acetate in hexane) to afford the title compound (II, Z-a-hydroxyl, fenprostalene) (4.6 mg, 65%) as an oil: IR(neat) 3449, 2924, 2859, 1960, 1728, 1599, 1462, 1379, 1273 cm$^{-1}$ $^1$H NMR δ 6.91–7.32 (m, 5 H), 5.74–5.67 (m, 2 H), 5.13–5.19 (m, 2 H), 4.52–4.54 (m, 1 H), 3.68 (s, 3 H).

What is claimed is:

1. A method for preparing a compound represented as formula II comprising the steps of:

reacting a compound represented as formula 1 in which R$^1$ and R$^2$ are acetyl, and P is hydrogen with a butyldimethylsilyloxypropylmagnesium bromide to give an allene compound represented as formula VIII, in the presence of copper iodide triethylphosphite complex;

reacting the allene compound represented as VIII with a tetra-nbutylammonium fluoride to give an allene compound represented as formula IX;

treating the compound represented as formula IX with potassium carbonate in methanol and pyridinium dichromate in methylene chloride;

reacting the resultant compound with pyridinium dichromate in N,N-dimethylformamide and methanol; and treating the resultant compound with a mixture of formic acid, H$_2$O and tetrahydrofuran

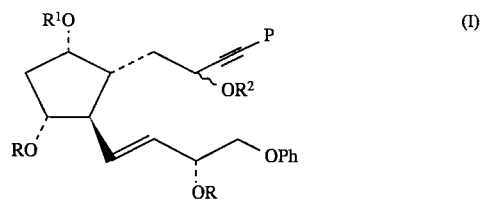

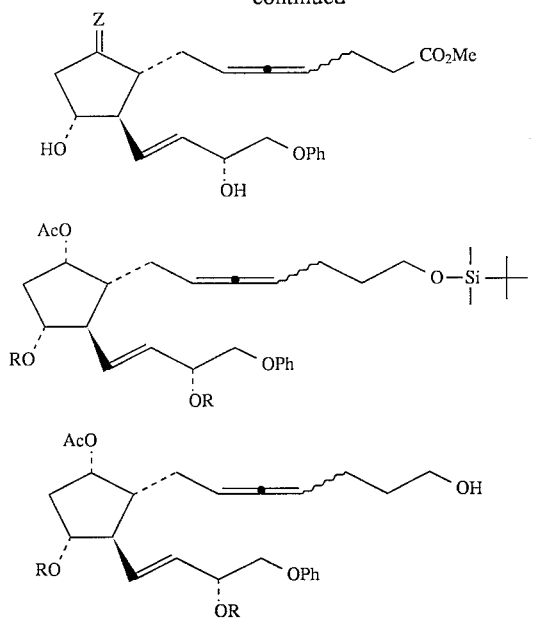

wherein R is tetrahydropyranyl, tetrahydrofuranyl, 2-ethoxyethyl, 3-t-butyldimethylsilyltriisopropylsilyl or triethylsilyl group; and Z is alpha-hydroxyl group or oxygen.

2. The method in accordance with claim 1, wherein the treating of the compound represented as formula IX with potassium carbonate and pyridinium dichromate is carried out by treating the compound represented as formula IX first with potassium carbonate and then with pyridinium dichromate in order.

3. The method in accordance with claim 1, wherein the treating of the compound represented as formula IX with potassium carbonate and pyridinium dichromate is carried out by treating the compound represented as formula IX first with pyridinium dichromate and then with potassium carbonate in order.

* * * * *